United States Patent [19]

Schmand et al.

[11] Patent Number: 5,744,638
[45] Date of Patent: Apr. 28, 1998

[54] PROCESS FOR THE PREPARATION OF HALOANTHRANILIC ACIDS

[75] Inventors: Horst Schmand, Bad Nenndorf; Bernd Kellermeier, Lindhorst; Günter Bartels, Burgwedel; Hans-Jürgen Schmidt, Seelze, all of Germany

[73] Assignee: Riedel-de Haen Aktiengesellschaft, Seelze, Germany

[21] Appl. No.: 372,865

[22] Filed: Jan. 13, 1995

Related U.S. Application Data

[63] Continuation of Ser. No. 158,048, Nov. 24, 1993, abandoned, which is a continuation of Ser. No. 997,547, Dec. 28, 1992, abandoned.

[30] Foreign Application Priority Data

Jan. 11, 1992 [DE] Germany ............... 42 00 512.4

[51] Int. Cl.$^6$ ................... C07C 229/00
[52] U.S. Cl. ............... 562/456; 562/458; 564/407
[58] Field of Search ............... 564/407; 562/458, 562/456

[56] References Cited

U.S. PATENT DOCUMENTS

| | | |
|---|---|---|
| 4,939,290 | 7/1990 | O'Neill. |
| 4,950,813 | 8/1990 | Doscher et al. ............ 560/127 |
| 5,064,958 | 11/1991 | O'Neill. |

FOREIGN PATENT DOCUMENTS

| | | |
|---|---|---|
| 0 306 804 | 3/1989 | European Pat. Off.. |
| 306 804 | 3/1989 | European Pat. Off.. |
| 370 686 | 5/1990 | European Pat. Off.. |
| 0 431 373 | 6/1991 | European Pat. Off.. |
| 244 207 | 3/1912 | Germany. |
| 33 01 868 | 7/1984 | Germany. |
| 0063323 | 6/1978 | Japan ............ 564/407 |
| 1143341 | 7/1986 | Japan ............ 564/407 |

OTHER PUBLICATIONS

Comptes Rendues, 202:1795–96 (1936).
Derwent Database, JP 4 356 449.
Methoden der Organischen Chemie, vol. 11, pp. 32–33 and 63–68.

Primary Examiner—Alan Siegel
Attorney, Agent, or Firm—Jay P. Friedenson

[57] ABSTRACT

The present invention relates to a process for the preparation of compounds of the general formula I

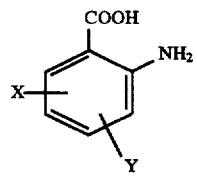

in which X and Y, independently of each other, represent hydrogen, fluorine, chlorine or bromine, but cannot simultaneously represent hydrogen, characterised in that compounds of the general formula II

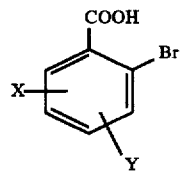

in which X and Y are defined as above, are reacted with aqueous ammonia under copper catalysis, and to intermediates for the preparation of compounds of the general formula I.

22 Claims, No Drawings

PROCESS FOR THE PREPARATION OF HALOANTHRANILIC ACIDS

This application is a continuation of application Ser. No. 08/158,048 filed Nov. 24, 1993 now abandoned, which in turn is a continuation of application Ser. No. 07/997,547 filed Dec. 28, 1992 now abandoned.

The present invention relates to a process for the preparation of haloanthranilic acids and to new intermediates for the preparation of haloanthranilic acids.

Haloanthranilic acids are valuable intermediates for the preparation of drugs (see for example U.S. Pat. No. 4,833, 270) or crop protection agents (see for example EP-A 360 417).

Processes for their preparation are already known. Thus, for example, the oxidation of halo-2-nitrotoluene with 30% strength aqueous nitric acid at elevated temperature and elevated pressure to give the corresponding benzoic acid and subsequent reduction of the nitro group is described in DE-A 34 09 244. However, due to the use of 30% strength aqueous nitric acid, reactors made from special and therefore very expensive materials are required for industrial application.

EP-A 342 849 describes the formation of halogenated compounds from haloanilines and subsequent oxidative alkaline ring-opening to give haloanthranilic acids. The disadvantage of this process is that all the steps are associated with considerable losses in yield. For example, the overall yield of 4,5-di-fluoroanthranilic acid starting from 3,4-difluoroaniline is according to U.S. Pat. No. 4,833,270 only 30% of theory. Finally, the ammonolysis of halophthalic anhydrides to give phthalimides followed by Hofmann rearrangement and degradation of the isocyanates to the haloanthranilic acids is also already known (CA 113 8916 w (1990) and Synthetic Communications 15 (6) p. 485–489 (1985)).

Since ring-opening of phthalimides is not selective and therefore two different end products may be produced, except when using 4,5-disubstituted phthalimides, this method is not generally applicable.

Furthermore, copper-catalysed ammonolysis of haloaryl compounds is already described in the literature. For example, 4-bromochlorobenzene may be converted selectively into 4-chloroaniline in this way in 10 hours in aqueous ammonia at 120° C. and about 10 bar pressure (P. H. Groggins: Unit Processes in Organic Synthesis (McGraw-Hill Book Co., Inc., New York, N.Y. 1952), Amination by ammonolysis p. 340–414, p. 377).

EP 51 783 describes the reaction of 1-amino-4-bromoanthraquinone-2-sulphonic acid in 25% strength ammonia at 80° C. and 15 bar pressure in the presence of catalytic amounts of $CuSO_4 \cdot 5H_2O$ to give the corresponding 1,4-diamino compound in a reaction time of 10 hours.

The ammonolysis of 3,5-dihydroxy-4-bromobenzoic acid or of an alkyl 3,5-dialkoxy-4-bromobenzoate in 35% strength ammonia solution at 118°–128° C. in 8–11 hours in the presence of $CuSO_4$ or CuO to give the corresponding 4-amino compounds is disclosed in HU 54 104.

The present invention relates to a process for the preparation of compounds of the general formula I

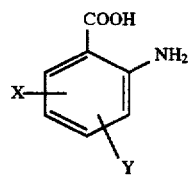

in which X and Y, independently of each other, represent hydrogen, fluorine, chlorine or bromine, but cannot simultaneously represent hydrogen, characterised in that compounds of the general formula II

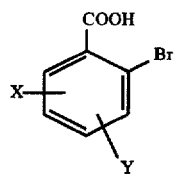

in which X and Y are defined as above, are reacted with aqueous ammonia under copper catalysis.

In the general formulae I and II, the substituents X and Y may be located in any positions on the benzene ring.

Preferred compounds of the general formula I are 4-fluoroanthranilic acid, 4-bromoanthranilic acid, 5-chloroanthranilic acid, 4-bromo-5-chloroanthranilic acid and 4,5-difluoroanthranilic acid.

Aqueous ammonia is preferably to be understood as meaning 20 to 40% strength ammonia solutions. Particularly preferred are commercially available 25% or 33% strength solutions.

Preferably, the ammonia is used in an excess of 1:3 to 1:6 above the stoichiometrically required amount of 3 molar equivalents, relative to the compound of the general formula II.

Copper catalysis is preferably to be understood as meaning the use of a copper(I) compound, particularly preferably of copper(I) oxide. The copper catalyst is preferably used here in a molar ratio of 0.09:1 to 0.15:1, relative to the compound of the general formula II.

Advantageously, the reaction according to the invention is carried out in an inert solvent. The choice of a suitable inert solvent in this case is mainly dictated by practical aspects, such as for example the solubility of the starting materials. Suitable inert solvents are for example ethyl acetate and isopropanol.

One preferred embodiment of the process according to the invention is carried out at temperatures of 20° to 110° C. and a pressure of 2 to 6 bar, preferably 4 bar.

A further embodiment of the process according to the invention is carried out at temperatures of 20° to 40° C. without the application of pressure. The reaction is complete after about 40 to 180 minutes when using this variant.

It is particularly preferable to complex the copper used with the aid of a suitable chelating agent at the end of the reaction and before working up the reaction mixture. A suitable chelating agent is especially ethylenediaminetetraacetic acid (EDTA).

Since, surprisingly, only the ortho bromine atom is ammonolysed in the process according to the invention and halogen substituents, including bromine, in other ring positions remain unaltered, the compounds of the general formula II may also be used in mixtures with for example isomeric compounds, such as may be produced under the conditions under which they are synthesised. For example, in a mixture of 2-bromo-4-fluorobenzoic acid and 4-bromo-2-fluoro-benzoic acid, only the former is converted and the latter may easily be separated from the desired anthranilic acid at a later stage.

Some of the compounds of the general formula II are known and may be prepared by known methods. For example, 2-bromo-4-fluorobenzoic acid may be obtained from 1-bromo-3-fluorobenzene by acetylation and oxidation of the 2-bromo-4-fluoroacetophenone which is produced (Recl. Trav. Chim. Pays-Bas, 83 p. 1142, 1146 (1964)). The oxidation of 2,4-dibromoacetophenone using potassium permanganate to give 2,4-dibromobenzoic acid is described in J. Karnatak Univ. 1 p. 36 (1956). According to J. Chem. Soc. 85, 1267 ff. (1904), 5-chloro-2-bromobenzoic acid may be obtained by nitric acid oxidation of 5-chloro-2-bromotoluene.

On the other hand, precursors of the general formula III

in which

R represents $CH_3$ and X' and Y', independently of each other, represent fluorine or chlorine or X' represents chlorine and Y' represents bromine or in which R represents COOH and X' and Y' represent fluorine, chlorine or bromine but cannot be identical, are new and are also a subject-matter of the present invention.

Preferably, R represents $CH_3$ or COOH and X' represents chlorine and Y' represents bromine.

Compounds of the general formula III in which R represents COOH are included under the general formula II and are direct precursors of the compounds of the general formula I in accordance with the process according to the invention.

Compounds of the general formula III in which R represents $CH_3$ may be converted into compounds of the general formula III in which R represents COOH by oxidation of the methyl group.

The compounds of the general formula III in which R represents $CH_3$ may be prepared by methods which are generally known from the chemistry of halogenated aromatic compounds.

Thus, for example, 4-bromo-5-chloroanthranilic acid may be prepared by the following scheme:

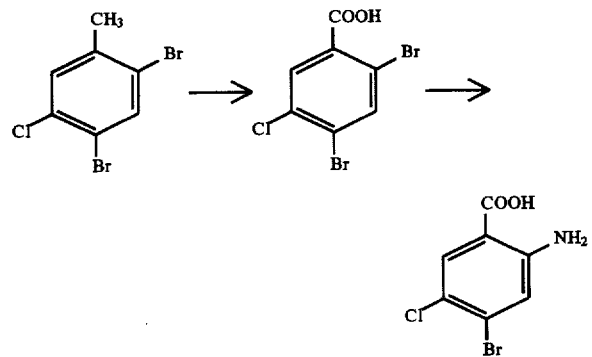

Here, the starting compound 5-chloro-2,4-dibromotoluene may be obtained, for example, by the bromination of 3-chlorotoluene or of 2-bromo-5-chlorotoluene.

EXAMPLES

1. Synthesis of 4-fluoroanthranilic acid 1.3 g of copper(I) oxide (0.009 mol) in 69 g (1 mol of $NH_3$) of an aqueous 25% strength ammonia solution is introduced into a glass flask under nitrogen. To this is added, at 25° C. over the course of 5 minutes and with stirring, a solution of 21.9 g (0.1 mol) of 2-bromo-4-fluorobenzoic acid in 18 g (0.27 mol) of 25% strength ammonia solution and 60 ml of ethyl acetate. The reaction is performed entirely under nitrogen. After addition of ammonium benzoate solution, the reaction temperature rises to about 40° C. The initially reddish copper(I) oxide suspension changes to a deep blue solution. After stirring for 1 hour at room temperature the reaction is complete. To complex the copper, 5.3 g of ethylenediaminetetraacetic acid is added to the batch, this is acidified to pH 3.1 with hydrochloric acid and the ethyl acetate is distilled off. The product is isolated at room temperature.

Yield: 14.6 g of 4-fluoroanthranilic acid, corresponding to 94% of theory.
HPLC: 99%
m.p.: 192°–194° C.
$^{13}C$ NMR (75 MHz, $^1H$ broad-band decoupled, DMSO-$d_6$) δ ppm 101.225 (d, $^2J(C—CF)$=24.3 Hz, arom. C) 102.38 (d,$^2J(C—CF)$=23.2 Hz, arom. C) 106.825 (arom. C) 134.18 (d, $^3J(C—CF)$=12 Hz, arom. C) 153.74 (d,$^3J(C—CF)$=13.36 Hz, arom. C) 165.75 (d, $^1J(C—CF)$=247 Hz, arom. C) 168.82 (—COOH)

2. Synthesis of 4-fluoroanthranilic acid 43.8 g (0.2 mol) of an isomeric mixture of 2,4-bromofluorobenzoic acid (HPLC: 76.7% 2-bromo-4-fluorobenzoic acid, 23.3% 4-bromo-2-fluorobenzoic acid) are dissolved in 160 g of ethyl acetate and placed in a 500 ml autoclave. To this are added one after the other 64 g (1.24 mol) of 33% strength ammonia solution, 18 g of water and 0.1 g ($7 \times 10^{-4}$ mol) of copper(I) oxide. The autoclave is flushed out with nitrogen, sealed and heated with stirring for 1 hour at 110° C., a pressure of at most about 4 bar being established. The mixture is left to react for 1 hour; the temperature falls to 80° C. and the pressure falls to 1 bar. The mixture is cooled, the pressure is released and the organic phase separates out on top. The aqueous phase is treated with 1.5 g of EDTA and adjusted to pH 3.1 with hydrochloric acid. The suspension is distilled in order to remove residual ethyl acetate and 26.2 g of an acid mixture are obtained, after the normal isolation procedure, consisting of 79.7% 2-amino-4-fluorobenzoic acid and 17.7% 4-bromo-2-fluorobenzoic acid, according to HPLC data. The slight differences in the composition of the product mixture and the starting material mixture may be caused by different sensitivities in the detection of 2-bromo-4-fluorobenzoic acid and 2-amino-4-fluorobenzoic acid.

Separation of 2-amino-4-fluorobenzoic acid and 4-bromo-2-fluoro-benzoic acid 26.2 g of the acid mixture are suspended in 166 ml of water. 80 g of 32% strength hydrochloric acid are added and the mixture is heated at 70° C. with stirring for 1 hour. The suspension is cooled to 20° C. and the insoluble 4-bromo-2-fluorobenzoic acid is filtered off under suction. This is washed with 50 ml of water and 9.4 g of 4-bromo-2-fluorobenzoic acid is obtained after drying. Content (from HPLC): 75%. The acid still contains 4-fluoroanthranilic acid. The hydrochloric acid filtrate is adjusted to pH 3.1 with sodium hydroxide solution and the precipitate is filtered off under suction at 15° C. The filter cake is washed until halide-free and dried.

Yield: 16.7 g (0.108 mol) of 4-fluoroanthranilic acid, corresponding to 54% of theory, relative to the benzoic acid mixture and corresponding to about 72% of theory relative to the 2-bromo-4-fluorobenzoic acid.

HPLC: greater than 99%

3. Synthesis of 4-bromoanthranilic acid 4.1 g (0.0287 mol) of copper(I) oxide in 143 g (2.1 mol of $NH_3$) of an aqueous 25% strength solution of ammonia are initially placed under nitrogen. A two-phase mixture consisting of 58 g (0.207 mol) of 2,4-dibromobenzoic acid in 56 g (0.8 mol of $NH_3$) of ammonia solution and 130 ml of ethyl acetate is added dropwise to this with stirring over the course of 30 minutes. The temperature rises from 18° to 40° C. during the addition. Stirring is continued for 15 minutes at 40° C. Copper is complexed with EDTA. The anthranilic acid is precipitated by acidifying to pH 3.1 with hydrochloric acid and isolated using normal laboratory procedure.

Yield: 40.9 g (0.189 mol) of 4-bromoanthranilic acid, which corresponds to 91.5% of theory.

HPLC: 97.3%

300 MHz $^1$H NMR (DMSO-$d_6$)

δ (ppm): 6.65 (dd, J=9 Hz, J=2 Hz, 1H) 6.98 (d, J=2 Hz, 1H) 7.6 (d, J=9 Hz, 1H)

4. Synthesis of 4-bromo-5-chloroanthranilic acid a) 799 g (5 mol) of bromine are added dropwise, at 0° C. with stirring, to 316.5 g (2.5 mol) of 3-chlorotoluene and 12.5 g of dry iron(III) chloride in 950 ml of 1-bromobutane. The addition takes place over 4 hours and stirring continues for about ½ hour at 0° C. After the evolution of hydrogen bromide subsides, 250 ml of water are added. After phase separation, the organic phase is washed with 250 ml of saturated sodium hydrogen carbonate solution. The 1-bromobutane is distilled off from the crude product which is obtained. 710 g (2.5 mol) of 5-chloro-2,4-dibromotoluene are obtained in a purity of 69.5% according to gas chromatography and an isomeric proportion of 18%.

Melting range: 70°–75° C.

By recrystallisation of the crude product from non-polar and dipolar aprotic solvents, such as e.g ligroin, petroleum ether, dichloromethane, 1,2-dichloromethane, isopropyl bromide or 1-bromobutane, 5-chloro-2,4-dibromotoluene is obtained in a yield of 79% of theory, relative to 3-chlorotoluene. The average purity is 97–99.8%, the melting range 92°–96° C.

$^1$H NMR (300 MHz in DMSO-$d_6$) δ values in ppm relative to TMS 2.30 (3 H, s) 7.79 (1 H, s) 7.87 (1 H, s)

b) 51.4 g (0.25 mol) of 2-bromo-5-chlorotoluene, 25 ml of dichloroethane and 1.5 g of iron powder are introduced into a round-bottomed flask. 40 g (0.25 mol) of bromine are added dropwise at 38°–40° C. with stirring, hydrogen bromide being evolved. The product precipitates out during the addition. The suspension is maintained by adding a further 35 ml of dichloromethane with vigorous agitation. Stirring is continued for 30 minutes after addition of the bromine. The crystal slurry is taken into solution at room temperature using 20 ml of dichloromethane and the iron powder is filtered off. The organic phase is concentrated by evaporation in a Rotavapor.58 g of 5-chloro-2,4-dibromotoluene is obtained, corresponding to 81.6% of theory relative to 2-bromo-5-chlorotoluene, purity (from gas chromatography): 91%, melting range 91°–95° C.

c) 5-chloro-2,4-dibromobenzoic acid

In a Hastelloy-C pressure apparatus, 299 g (1.05 mol) of 5-chloro-2,4-dibromotoluene (purity 97% according to gas chromatography) in 3000 g acetic acid is oxidised to 5-chloro-2,4-dibromobenzoic acid using compressed air, with catalysis by 130.8 g of cobalt(II) acetate.4$H_2O$, 4.4 g of manganese(II) acetate.4$H_2O$ and 35 g of sodium bromide, at a pressure of 5 bar and a reaction temperature of about 130° C. over the course of 6 hours. After the reaction has finished 2 l of acetic acid is distilled off under atmospheric pressure and the 5-chloro-2,4-dibromobenzoic acid is precipitated with 4 l of water. The crude product is then heated to 70° C in 1.5 l of water and 150 ml of 32% strength sodium hydroxide solution to make a solution, cooled and the product precipitated in the filtrate at pH 1 with 180 l of 32% strength hydrochloric acid. After filtering under suction, washing and drying, 247.7 g of 5-chloro-2,4-dibromobenzoic acid are obtained, corresponding to 75% of theory.

HPLC: 99.8%

$^1$H NMR (300 MHz, DMSO-$d_6$) δ values in ppm 8.05 (1H, s); 8.08 (1H, s) 12.0–15.7 (1H, broad H/D)

$^{13}$C NMR (75 MHz, $^1$H broad-band decoupled, DMSO-$d_6$) δ ppm 119.14 (arom. C) 125.218 (arom. C) 131.49 (arom. C) 132.9175 (arom. C) 134.36 (arom. C) 137.98 (arom. C) 165.50 (—COOH)

d) 4-bromo-5-chloroanthranilic acid 2.8 g (0.0196 mol) of copper(I) oxide are suspended in 120 ml (corresponding to 1.6 mol of $NH_3$) of 25% aqueous ammonia solution under nitrogen. To this is added dropwise, at 25° C. with stirring and over the course of 40 minutes, a suspension of 63.2 g (0.2 mol) of 5-chloro-2,4-dibromobenzoic acid, 160 ml (corresponding to 2.14 mol of $NH_3$) of 25% strength aqueous ammonia solution and 180 ml of ethyl acetate, with the exclusion of oxygen. The temperature rises to about 35° C. during the addition. Stirring is continued for 2¼ hours at 30° C. Finally, 11.6 g (0.04 mol) of ethylenediaminetetraacetic acid is added to the mixture and the pH is adjusted to 3.1 by acidifying with hydrochloric acid. The ethyl acetate is distilled off at 90° C., the suspension is stirred at room temperature, and the anthranilic acid is filtered off under suction and washed. 48.2 g of 4-bromo-5-chloroanthranilic acid is obtained as a pale-brown powder, corresponding to 96.2% of theory relative to 5-chloro-2,4-dibromobenzoic acid.

Purity (HPLC): 95%

$^{13}$C NMR (75 MHz, $^1$H broad-band decoupled in DMSO-$d_6$) δ values in ppm arom.=aromatic 110.494 (arom. C) 117.423 (arom. C) 120.652 (arom. C) 126.907 (arom. C) 131.726 (arom. C) 150.743 (arom. C) 167.913 (—COOH)

5. Synthesis of 5-chloroanthranilic acid

The same procedure as in example 1 was used.

Yield: 97% of theory

HPLC: 90% m.p.: 233°–235° C.

6. Synthesis of 4,5-difluoroanthranilic acid

The same procedure as in example 1 was used.

Yield: 91% of theory

HPLC: 99% m.p.: 180°–182° C.

We claim:

1. Process for the preparation of compounds of the general formula I

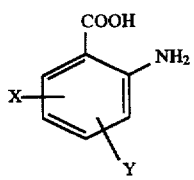

in which X and Y, independently of each other, represent hydrogen, fluorine, chlorine or bromine but cannot simultaneously represent hydrogen, comprising reacting compounds of the general formula II

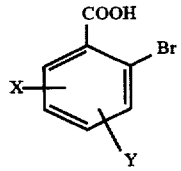

in which X and Y are defined as above, with aqueous ammonia under copper catalysis at atmospheric pressure.

2. Process according to claim 1, wherein the aqueous ammonia used is a 20 to 40% strength.

3. Process according to claim 2, wherein the aqueous ammonia used is 25 to 33% strength.

4. Process according to claim 1, wherein ammonia is used in an excess of 1:3 to 1:6 above the stoichiometrically required amount of 3 molar equivalents, relative to the compound of the general formula II.

5. Process according to claim 1, wherein the copper catalyst used is a copper(I) compound.

6. Process according to claim 5, wherein the copper catalyst used is copper(I) oxide.

7. Process according to claim 1, wherein the copper catalyst is used in a molar ratio of 0.09:1 to 0.15:1, relative to the compound of the general formula II.

8. Process according to claim 1, wherein the process is carried out at temperatures of 20°–40° C. without the application of pressure.

9. Process according to claim 1, wherein the compounds of general formula I are selected from the group consisting of 4-fluoroanthranilic acid, 4-bromoanthranilic acid, 5-chloroanthranilic acid, 4-bromo-5-chloroanthranilic acid and 4,5-difluoroanthranilic acid.

10. Process according to claim 1, wherein the reaction is carried out in an inert solvent.

11. Process according to claim 10, wherein the inert solvent is ethyl acetate or isopropanol.

12. Process for the preparation of compounds of the general formula

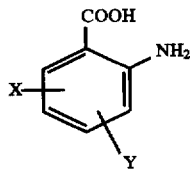

in which one of the substituents X and Y, represent bromine and the other represents hydrogen, fluorine, chlorine or bromine, consisting essentially of reacting compounds of the general formula II

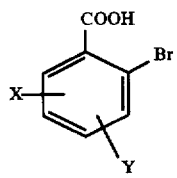

in which X and Y are defined as above, with aqueous ammonia under copper catalysis at atmospheric pressure.

13. The process as claimed in claim 1, wherein at least X or Y is bromine.

14. The process as claimed in claim 13, wherein X and Y are bromine.

15. Process for the preparation of compound of the general formula I

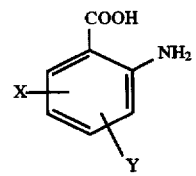

in which X and Y, independently of each other, represent hydrogen, fluorine, chlorine or bromine, but cannot simultaneously represent hydrogen, consisting of reacting compounds of the general formula II

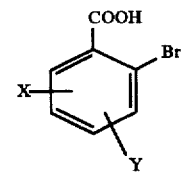

in which X and Y are defined as above, with aqueous ammonia under copper catalysis at atmospheric pressure.

16. The process as claimed in claim 1, wherein the process consists of reacting compounds of the formula II

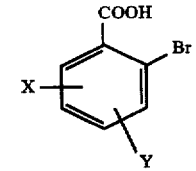

in which X and Y are defined in claim 1, with aqueous ammonia under copper catalysis at atmospheric pressure.

17. The process as claimed in claim 12, wherein the process consists of reacting compounds of the general formula II

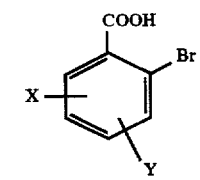

in which X and Y are defined in claim 12, with aqueous ammonia under copper catalysis at atmospheric pressure.

18. Process according to claim 1, wherein the compounds of the general formula II are in a mixture including isomers or other compounds of the same general formula II except that bromo at the 2- position has been replaced and further comprising the step of separating the compound of the general formula I as a product.

19. Process according to claim 1, wherein the reaction is carried out at a temperature in the range of 20° to 110° C. and at a pressure in the range of 2 to 6 bar.

20. Process according to claim 1, wherein the reaction is carried out at a temperature in the range of 20° to 40° C. and is completed after about 40 to 180 minutes.

21. Process according to claim 1, further comprising the step of complexing the copper with a chelating agent after the reaction is complete.

22. Process according to claim 21, wherein the chelating agent is EDTA.

* * * * *